US00PP31192P2

(12) United States Plant Patent
Worthington et al.

(10) Patent No.: US PP31,192 P2
(45) Date of Patent: Dec. 10, 2019

(54) NECTARINE TREE NAMED 'EFFIE'

(50) Latin Name: *Prunus persica*
Varietal Denomination: Effie

(71) Applicant: THE BOARD OF TRUSTEES OF THE UNIVERSITY OF ARKANSAS, Little Rock, AR (US)

(72) Inventors: Margaret Worthington, Fayetteville, AR (US); John R. Clark, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 16/350,803

(22) Filed: Jan. 14, 2019

(51) Int. Cl.
*A01H 5/00* (2018.01)

(52) U.S. Cl.
USPC ..... Plt./188

(58) Field of Classification Search
USPC ..... Plt./188
CPC ..... A01H 5/00
See application file for complete search history.

(56) References Cited

PUBLICATIONS

Effie Nectarine Worthington et al. HortSience 53(6) 897-901 2018.*
University of Arkansas introduces 'Effie' the nectarine Chris Roger Aug. 14, 2018.*

* cited by examiner

*Primary Examiner* — Annette H Para
(74) *Attorney, Agent, or Firm* — Quarles & Brady LLP

(57) ABSTRACT

Description and specification of a new and distinct nectarine tree cultivar named 'Effie' which originated from a hand-pollinated cross of Ark. 720 nectarine (female; non-patented) x Ark. 747 peach (male; non-patented) made in 2004. This new nectarine cultivar can be distinguished by its firm fruit with non-melting white flesh, late ripening season, medium size, attractive appearance, high red skin color, excellent fruit quality, good flavor, and resistance to bacterial spot disease.

2 Drawing Sheets

Latin name: *Prunus persica.*
Varietal denomination: 'Effie'.

BACKGROUND

A new and distinct nectarine cultivar named 'Effie' is described herein. The new cultivar originated from a hand-pollinated cross of Ark. 720 nectarine (female parent; non-patented; unreleased breeding genotype) x Ark. 747 peach (male parent; non-patented; unreleased breeding genotype) made in 2004 near Clarksville, Ark. This new cultivar was selected in 2008 for its potential as a fresh-market nectarine in Arkansas and the mid- to upper-southern United States. 'Effie' can be distinguished by its distinctly crisp non-melting flesh, mid-season ripening, medium size, attractive appearance, high red skin color, excellent white nectarine flavor, postharvest performance, and resistance to bacterial spot disease.

SUMMARY OF THE INVENTION

The new and distinct nectarine cultivar originated from a hand-pollinated cross of Ark. 720 nectarine (female parent; non-patented; unreleased breeding genotype) x Ark. 747 (male parent; peach; non-patented; unreleased breeding genotype) made in 2004 near Clarksville, Ark. The seeds resulting from this controlled hybridization were germinated in a greenhouse in the late winter 2004/early spring of 2005 and planted in a field near Clarksville, Ark. The seedlings fruited during the summer of 2008 and one nectarine seedling, designated Ark. 805, was selected for its crisp non-melting flesh, mid-season ripening, attractive appearance, excellent white nectarine flavor, and resistance to bacterial spot disease.

During 2008, the original plant selection was propagated asexually, at the above-noted location, by budding onto standard peach rootstock cultivar 'Lovell' (non-patented) and a test plot of two plants was established. Subsequently, larger test plantings have been established with asexually multiplied plants at two additional locations in Arkansas (near Clarksville and Hope, Ark.). At each location propagation was by budding onto the standard peach rootstock cultivar 'Guardian' (Okie et al., 1994) from buds collected at the Clarksville, Ark. test plot. No incompatibility with 'Lovell' or 'Guardian' peach rootstocks has occurred following budding. During all asexual multiplication, the characteristics of the original plant have been maintained and no aberrant phenotypes have appeared.

The new cultivar has been named 'Effie'.

BRIEF DESCRIPTION OF THE PHOTOGRAPHS

The accompanying photographs show typical specimens of the new cultivar in color as nearly true as it is reasonably possible to make in a color illustration of this character.

DETAILED DESCRIPTION OF THE NEW CULTIVAR

Figure 1:
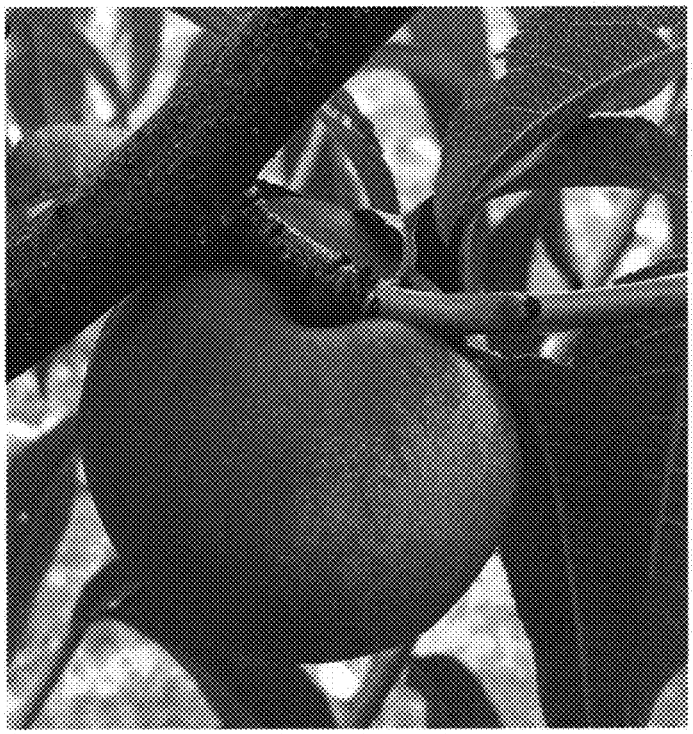
FIG. 1 is a photograph of mature fruit on a tree of 'Effie' at eight years of age.
Figure 2:
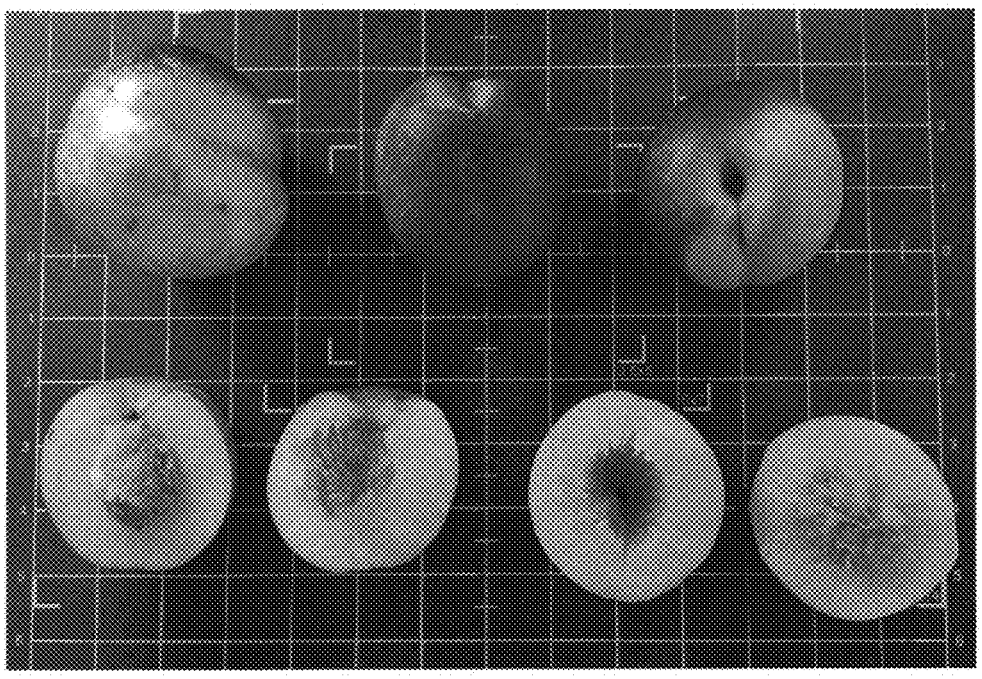
FIG. 2 is a photograph of whole and longitudinally cut fruits of 'Effie' at maturity at eight years of age.
Figure 3:
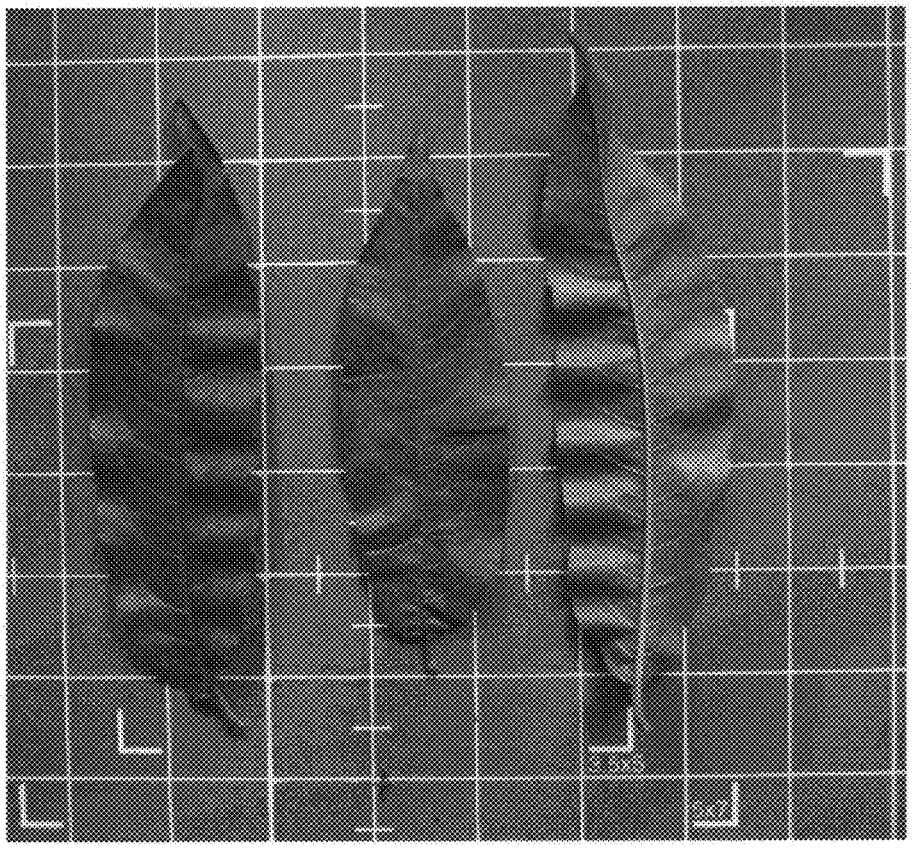
FIG. 3 is a photograph of the adaxial and abaxial sides of mature 'Effie' leaves at eight years of age.

Plants and fruit of this new cultivar differ phenotypically from its parents. While 'Effie' has white, clingstone, non-melting flesh, its female parent, Ark. 720, had yellow, clingstone, melting flesh. 'Effie' is also easily distinguished from its male parent, Ark. 747, in that it is a nectarine with glabrous skin, while Ark. 747 was a peach selection with pubescent skin. The acidity of 'Effie' fruit is intermediate between its high acid female parent, Ark. 720, and low acid male parent, Ark. 747. Both the parents and the new cultivar are the genus and species *Prunus persica*.

Trees of the new cultivar are moderately vigorous, productive, standard in size, well-branched and symmetrical with an upright to semi-spreading growth habit, comparable to other peach and nectarine trees. Trees express a high level of resistance to both foliar and fruit infection of bacterial spot [*Xanthomonas campestris* pv. *pruni* (Smith) Dye] but in some years do not show complete immunity to this disease. The new cultivar blooms in the spring on approximately the same date as 'Amoore Sweet' (U.S. Plant Pat. No. 26,367), 'Arrington' (U.S. Plant Pat. No. 12,641), 'Bowden' (U.S. Plant Pat. No. 26,402), and 'Bradley' (U.S. Plant Pat. No. 12,620). No winter cold injury has been observed on wood or buds of the new cultivar in Arkansas tests where minimum temperatures have reached 2° F. (−17° C.) during evaluation. Chilling requirement to break dormancy is estimated to be 800 hours below 45° F. (7° C.).

Fruit of the new cultivar ripens mid-season, averaging 7-10 days after 'Amoore Sweet' and 'Bowden' and two weeks after 'Arrington' and 'Bradley' reference nectarine cultivars. Average first ripening date is July 16 in west-central Arkansas (Clarksville). In 2016, 40% (⅖) of a sample group of fruit had split pits. Fruit yields have been good and are comparable to the nectarine cultivars 'Amoore Sweet' and 'Bowden'.

The fruit is round in shape. Fruits are attractive with an average 84% bright red blush. Fruit finish is comparable to 'Amoore Sweet', with fewer blemishes on average than 'Bowden'. The fruit skin has no pubescence, a major difference between peaches and nectarines. The flesh of the fruit is white in color with no red flecking or discoloration. Flesh is of the non-melting type and is very firm at maturity. The fruit is a clingstone, in that the flesh adheres to the pit. Fruit size is medium, averaging 143 g, slightly less than 'Amoore Sweet' (172 g), 'Bowden' (166 g), and 'Bradley' (166 g), but larger than 'Arrington' (118 g). The fresh fruit has excellent white nectarine flavor and was rated highly in evaluations. Fruits average 16.1% soluble solids, higher than 'Amoore Sweet' (14.4%), 'Arrington' (14.8%), 'Bowden' (13.1%), and 'Bradley' (12.5%). The flavor is sweet with moderate acidity. The acidity level of 'Effie' was 0.44% malic acid compared to 'Amoore Sweet' with 0.22% and 'Bowden' with 0.64%.

The following is a detailed description of the botanical and pomological characteristics of the subject nectarine. Color data are presented in Royal Horticultural Society Colour Chart designations (1986 2$^{nd}$ edition). Where dimensions, sizes, colors and other characteristics are given, it is to be understood that such characteristics are approximations of averages set forth as accurately as practical.

Plants used for botanical data were eight years old and grown on a fine sandy loam soil with trickle irrigation near Clarksville, Ark. Trees were trained to an open-center training system and dormant pruned annually. The exception to this is that yield data was collected on trees four years old and trained to a perpendicular V training system. Fruits on all trees were thinned to approximately 6-8 inches between fruits 4-5 weeks after full bloom. The trees were fertilized near budbreak (late March on average) with complete or nitrogen fertilizer. Weeds were controlled with pre- and post-emergence herbicides. Routine commercial fungicide and insecticide applications were applied to the trees, but no bactericides (for control of bacterial diseases such as bacterial spot disease) were applied. The descriptions reported herein are from specimens grown near Clarksville, Ark.

Plant:

*Size*.—Mature trees (eight years of age) average 3.6 m to 3.8 m in height and 4.8 to 5.9 m in spread or width, and a semi-upright growth habit, as grown on 'Lovell' rootstock using an open-center training system commonly used on peaches. Tree size is comparable to that of the 'Amoore Sweet' and 'Bowden' cultivars.

*Growth*.—Vigorous, symmetrical form, good canopy development. Vigor comparable to that of the 'Amoore Sweet' and 'Bowden' cultivars.

*Productivity*.—Good productivity and consistent from year to year. Crop load ratings averaged 7.7 on a 10-point scale. These ratings were comparable to or higher than those for 'Arrington' (7.7) and 'Bradley' (7.4), though slightly lower than 'Amoore Sweet' (8.4) and 'Bowden' (8.4). Yields from a 2014-planted replicated trial evaluated in 2015-2017 averaged 6.0 kg/tree for 'Effie', compared to 8.8 kg/tree for 'Amoore Sweet', and 8.6 kg/tree for 'Bowden'.

*Cold hardiness*.—Wood and dormant buds hardy to 2° F. (−17 ° C.). This was the coldest temperature that the trees were exposed to at the test site, but hardiness may exceed this temperature.

*Disease resistance*.—Leaves and fruit resistant but not immune to bacterial spot under growing conditions where bacterial spot infection is often very severe on susceptible genotypes. No bactericides were used in the development or evaluation of the instant cultivar. Percent of harvested fruit with bacterial spot symptoms was less than that of 'Amoore Sweet' and 'Bowden'. A commercial fungicide program was utilized in orchards used in the development and evaluation of the instant cultivar, thus no resistance to brown rot (*Monilinia fructicola* (G. Winter) Honey) or scab (*Fusicladium carpophilum* (Thum.) Oudem), the other common diseases at Clarksville, Ark., were determined.

*Insect resistance*.—Insecticides were applied to orchards used in the development of the instant cultivar to control the common insects at the location including oriental fruit moth (*Grapholita molesta* (Busck)), plum curculio (*Conotrachelus nenuphar* (Herbst)), stinkbug (*Halyomorpha halys* (Stal); *Euschistus servus* (Say); *Acrosternum hilare* (Say); *Nezara viridula* (Linnaeus); *Thyanta* spp.), tarnished plant bug (*Lygus lineolaris* (Palisot de Beauvois)), lesser peach tree borer (*Synathedon pictipes* (Grote & Robinson)), and greater peach tree borer (*Synan-*

*thedon exitiosa* (Say)). Therefore no insect resistance was determined in the testing of the instant cultivar.

Foliage/shoots/branches:

*Shoots*.—Smooth. Dormant-season shoot (branch): length 59.2 cm; diameter at base 0.5 cm; diameter at midpoint 0.4 cm; diameter at terminal 0.3 cm. Dormant-season shoot color top: Red Purple Group 60B; bottom: Green Group 143C

*Leaves*.—Simple, alternate, glabrous, lanceolate, petiolate, and deciduous. Venation pinnate; base acute; terminal or apex acuminate; margin serrated. Mature leaf size: length 12.0 cm; width midpoint 3.7 cm. Leaf serrations 4.8/cm. Mature leaf color: abaxial — Green Group (137C); adaxial — Green Group (137A). Young leaf color: abaxial — Green Group (138B); adaxial — Green Group (137C); anthocyanin not present on abaxial or adaxial side of young leaves on midrib or other location. Petiole length — mature leaf: 0.88 cm, petiole width: 1.48 mm; petiole texture: smooth no pubescence; petiole strength: average to strong. Leaf glands: reniform, average of 1.6 per leaf, located at base of leaf blade at top of petiole. Leaf glands are 0.08 cm in width and 0.07 cm in length. Stipule length: 1.07 cm.

*Buds*.—Number of leaf buds per 15 cm: 6.8, evenly distributed along the shoot. Number of flower buds per 0-15 cm from terminal: 11.8. Mature shoot internode length: base 1.9 cm, midpoint 2.5 cm, terminal 1.6 cm.

Bark (of mature trunk of tree):

*Color*.—Greyed-Green Group (196B).

*Texture*.—Rough.

Trunk:

*Diameter*.—14.9 cm (at 25 cm above ground level).

Flower buds: Dormant flower bud length 0.6 cm and diameter 0.3 cm and color Red Purple Group (59A); dormant buds swell and expand in late winter and increase in size during this expansion to fully open flowers.

Flowers: Bloom occurs prior to vegetative bud break; solitary to occasional double individual flowers at a single node; perfect; self-fertile.

*Date of bloom*.—First, Julian 77 (March 17); Full, Julian 80 (March 20). Full bloom for 'Amoore Sweet' (March 18) and 'Bowden' (March 20).

*Size*.—Diameter fully open 2.3 cm.

*Type*.—Non-Showy.

*Color*.—Adaxial/abaxial: — Front and back same color-but edges and center different. Edge: Red Purple Group (63B); Center: Red Purple Group (63C).

*Petals per flower*.—5.8.

*Petal dimensions*.—Length 12.3 mm; width 7.3 mm; texture smooth.

*Length of pistil*.—1.8 cm.

*Stamens*.—Average 44.6/flower with pollen present, fertile and abundant.

*Ovary*.—Smooth. Grayed-Green Group (193A).

Fruit:

*Size*.—Medium, avg. 177 g. Similar to 'Amoore Sweet' (173 g) and Bowden (173 g). Diameter stem end 4.7 cm, equator 6.0 cm, blossom end 2.6 cm; length base to apex 7.3 cm.

*Shape*.—Round, symmetrical with no tip.

*Skin*.—Smooth (nectarine), attractive; ground color Yellow-Orange Group (20B), with red blush (Red Group 53A) covering about 84% of surface on average.

*Flesh*.—Color Yellow Group (4D); clingstone; uniform non-melting without rubbery texture. Firmness rating of 8.7 (based on 1 to 10 scale with 10 being very firm) which was comparable to 'Amoore Sweet' (8.9) and 'Bradley' (8.7). Excellent eating quality; distinct white nectarine flavor, sweet, and mild-acid.

*Pedicel length*.—0.3 cm.

*Pedicel diameter*.—0.3 cm.

*Pedicel color*.—Grayed-Orange Group (164A).

*Pedicel strength*.—Strong; holds on well.

*Ripe date*.—July 8 (Julian 190) in west-central Arkansas; 'Amoore Sweet' and 'Bowden' cultivars ripen 7 days earlier. Ripening of individual fruit is uniform.

*Tendency of pit to split*.—No split pits most years. In 2016, two of five fruit evaluated had split pit.

*Soluble solids*.—13.9%.

*Fruit juice ph*.—3.63.

*Fruit juice titratable acidity*.—0.44% malic acid.

*Fruit glossiness*.—Weak.

*Storage performance*.—Overall ranking for 0-3 weeks of storage for 'Effie' was 4.0, the same as 'Bowden' and higher than 'Amoore Sweet' (3.8) on a 5-point scale with 5 being exceptional storage. After three weeks of storage, 'Effie' developed negligible mealiness (dry, gel texture) and maintained a high level of juiciness.

Pit/stone:

*Size*.—Length 4.5 cm; diameter (midpoint) 2.9 cm.

*Shape*.—Slightly oblong with deep furrowing and pitting.

*Color*.—Greyed-Orange Group (165B).

Kernel:

*Size*.—Length 1.9 cm; diameter varies with dryness of the kernel but is up to 1.3 cm.

*Shape*.—Oval.

*Color*.—Grayed-Orange Group (165B).

Uses: Fresh consumption, not evaluated for drying or other uses.

THE CULTIVAR

The outstanding characteristics of 'Effie' are attractive and flavorful white nectarine fruit, crisp texture and post-harvest storage potential, bacterial spot resistance, and later ripening season compared to other nectarine releases.

LITERATURE CITED

Okie, W. R., T. G. Beckman, A. P. Nyczepir, G. L. Reighhard, W. C. Newall, and E. I. Zehr. 1994. BY520-9, a peach rootstock for the southeastern United States that increases scion longevity. HortScience 29(6): 705-706.

We claim:

1. A new and distinct cultivar of peach tree named 'Effie', substantially as illustrated and described.

* * * * *